United States Patent [19]

de Ruiter

[11] Patent Number: Plant 5,976

[45] Date of Patent: May 12, 1987

[54] ROSE PLANT—RUIREDRO VARIETY

[75] Inventor: Gijsbert de Ruiter, Hazerswoude, Netherlands

[73] Assignee: The Conard-Pyle Company, West Grove, Pa.

[21] Appl. No.: 624,739

[22] Filed: Jun. 26, 1984

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Burns, Doane, Swecker & Mathis

[57] ABSTRACT

A new and distinct variety of Miniature rose plant is provided which resulted as a seedling from a planned hybridization program. The new variety exhibits very long-lasting flowers of a deep red coloration which are borne on a very compact plant. The new variety is very well-adapted to greenhouse forcing as a flowering pot plant as well as to general outdoor usage.

1 Drawing Figure

SUMMARY OF THE INVENTION

The present invention relates to a new and distinct variety of Miniature rose plant which originated as a seedling in my breeding program which was carried out in The Netherlands.

The object of my breeding program was to create a new variety of the Miniature rose class having attractive red flowers on a compact, well-balanced plant which is especially well-suited to greenhouse forcing as a flowering pot plant. This objective was successfully achieved, and the new variety exhibits a combination of characteristics which distinguish it from all other varieties of the Miniature rose class of which I am aware. The new variety also was found to grow well out-of-doors in the garden.

The following combination of characteristics is observed in the new variety:

(a) forms flowers of a medium deep red coloration which are of unusually long duration, (b) exhibits a well-balanced, compact and vigorous growth habit which is extremely floriferous, (c) exhibits an excellent aptitude for greenhouse forcing as a flowering pot plant, and (d) exhibits a very good comportment when used as an outdoor garden plant.

Asexual reproduction by cuttings and grafting has been accomplished in Hazerswoude, The Netherlands, and at West Grove, Pa., USA. Succeeding propagations have shown that the unique combination of characteristics is fully established and is transmitted to successive generations.

The new variety has been named the Ruiredro variety.

BRIEF DESCRIPTION OF THE PHOTOGRAPH

The accompanying photograph shows typical specimens of my new variety of Miniature rose plant during February as depicted in color as true as is reasonably possible to make the same in a color photograph of this nature. The specimens illustrated were grown in a greenhouse in an artificial soilless medium at West Grove, Pa., USA. The specimens illustrated tend to exhibit a more orange-red blossom coloration near Red Group 44B of The R.H.S. Colour Chart when observed during February under greenhouse conditions than those described hereafter by reference to The R.H.S.

Colour Chart when observed during May in a greenhouse at the same location.

DETAILED DESCRIPTION

The plants hereafter were grown on their own roots in four inch pots containing an artificial soilless medium while present in a greenhouse during early May at West Grove, Pa., USA. The month of blossoming has been found to influence the blossom coloration to some degree.

The chart utilized in the identification of the colors is that of The Royal Horticultural Society (R.H.S. Colour Chart).

Class: Miniature.

Plant:

*Bearing.*—A low growing shrub with compact growth.

Branches:

*Color.*—Young stems: ranges from Yellow-Green Group 144A to 144B. mature wood: Green Group 143A.

*Thorns.*—Shape — upper edge: straight. shape — under edge: concave. shape — base: elliptical. quantity: few. color on young stems: Yellow Group 4C. color on mature wood: Yellow Group 4B at the tip and under side, with the base and upper edge commonly showing tones of Red-Purple Group 60D.

Leaves:

*Petioles.*—Inner surface: Yellow-Green Group 144A. Younger petioles commonly have a tinge of Red-Purple Group 60D. outer surface: Yellow-Green Group 144A.

*Thorns.*—Number: commnly range from approximately 2 to 6 per leaf with the average number being 3. color: Yellow Group 11C.

*Leaflets.*—Number: 3 to 7 per leaf. shape: elliptical to ovate in shape with acute to obtuse tip and acute to rounded base. teeth: edges are serrulate. size: approximately 1 to 2.5 cm. in length (e.g. approximately 1.5 cm. on average), and approximately 0.5 to 1.75 cm. in width (e.g. approximately 1 cm. on average).

*Color.*—Young foliage: upper surface: Green Group 137B. under surface: Geeen Group 138B with tinges of Red-Purple Group 60B. adult foliage: upper surface: Green Group 137A. under surface: ranges between Green Group 137C and Green Group 138B.

Inflorescence:

*Number of flowers.*—The majority of the flowers are borne singly; however, there commonly are some clusters of flowers which number approximately 2 to 4 per cluster.

*Peduncle.*—Color: Yellow-Green Group 144A.

*Bud.*—Shape: before the opening it has a rounded base and a pointed tip, and after opening it has a rounded base and a flat top. color when opening: upper surface: Red Group 53A. under surface: Red Group 53C.

*Flower.*—Shape: the petals join together at a center point to form a round flat bloom, and as the flower ages the outer petals show a tendency to point downward. diameter: approximately 2 to 3 cm. with the average being closer to 3 cm. color during opening: inside: petal tip is Red Group 46A blending to Red Group 53B at the base. outside: petal tip is Red Group 53C blending to Red Group 53D at the base. color when fully open: inside: petal tip is Red Group 46A blending to Red Group 53A at the base. outside: petal tip is Red Group 53B blending to Red Group 53D at the base. fragrance: none. lasting quality: average.

Development:

*Vegetation.*—Vigorous.

*Blossoming.*—Profuse.

*Resistance to disease.*—Good.

I claim:

1. A new and distinct variety of Miniature rose plant, substantially as illustrated and described, having the following combination of characteristics:

(a) forms flowers of a medium deep red coloration which are of unusually long duration, (b) exhibits a well-balanced, compact and vigorous growth habit which is extremely floriferous, (c) exhibits an excellent aptitude for greenhouse forcing as a flowering pot plant, and (d) exhibits a very good comportment when used as an outdoor garden plant.

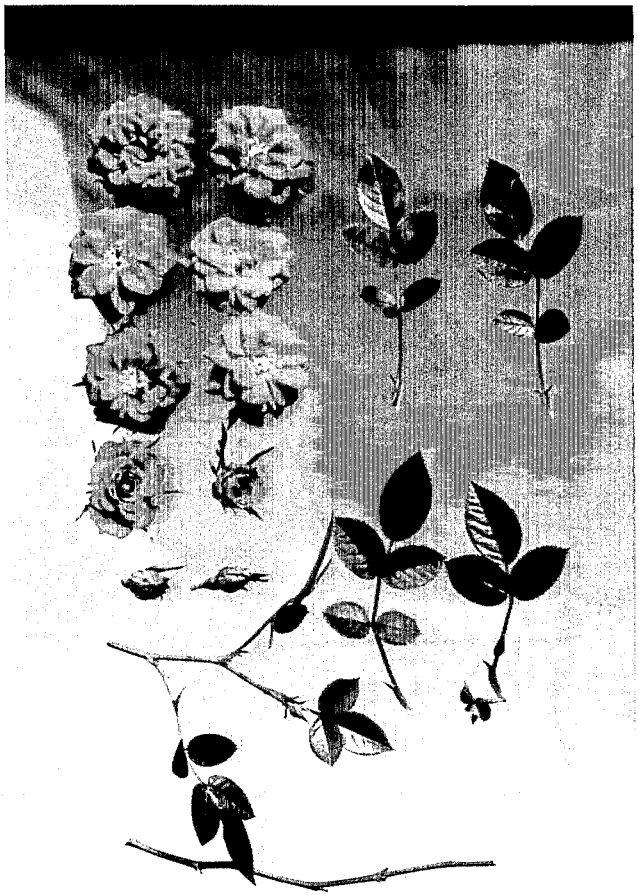

* * * * *